United States Patent
Zaugg et al.

(10) Patent No.: US 7,998,696 B2
(45) Date of Patent: Aug. 16, 2011

(54) CELL ASSAY KIT AND METHOD

(75) Inventors: Frank Zaugg, Redwood City, CA (US); Renee Tobias, San Jose, CA (US); Silvia McManus-Munoz, Castro Valley, CA (US); Peter Kernen, Redwood City, CA (US); Laurence Ruiz-Taylor, Belmont, CA (US); Peter Wagner, Menlo Park, CA (US)

(73) Assignee: Zyomyx, Inc., Hayward, CA (US)

( * ) Notice: Subject to any disclaimer, the term of this patent is extended or adjusted under 35 U.S.C. 154(b) by 348 days.

(21) Appl. No.: 12/329,380

(22) Filed: Dec. 5, 2008

(65) Prior Publication Data
US 2009/0148869 A1 Jun. 11, 2009

Related U.S. Application Data

(60) Provisional application No. 60/992,624, filed on Dec. 5, 2007.

(51) Int. Cl.
| | | |
|---|---|---|
| *G01N 33/00* | (2006.01) | |
| *G01N 7/00* | (2006.01) | |
| *G01N 1/18* | (2006.01) | |
| *F04B 19/00* | (2006.01) | |
| *B01L 3/00* | (2006.01) | |

(52) U.S. Cl. ........... 435/7.24; 435/2; 435/7.2; 435/7.23; 435/286.5; 435/287.1; 435/287.2; 435/288.6; 436/518; 436/523; 436/524; 436/526; 436/528; 436/536; 436/538; 436/148; 436/177; 422/70; 422/72; 422/412; 422/415; 422/506; 422/522; 422/523

(58) Field of Classification Search ............... 435/2, 7.2, 435/7.23, 7.24, 287.2, 286.5, 287.1, 288.6; 436/518, 523, 524, 526, 528, 536, 538, 56, 436/165, 177, 148; 422/70, 101, 72, 412, 422/415, 506, 522, 523

See application file for complete search history.

(56) References Cited

U.S. PATENT DOCUMENTS 4,027,660 A 6/1977 Wardlaw et al.
(Continued)

FOREIGN PATENT DOCUMENTS

DE 3925093 A1 1/1991

OTHER PUBLICATIONS

"TPP Premium Quality 15ml & 50ml Centrifuge Tubes" XP002539217, Internet Article, Jun. 19, 2007 Retrieved from the Internet: URL:http//web.archive.org/web/20070619004830/http://216.15.207.230/cat/prodprice2_Detail.cfm?ID=669>, paper filed only.

(Continued)

*Primary Examiner* — Gail R Gabel
(74) *Attorney, Agent, or Firm* — King & Spalding LLP; Peter J. Dehlinger

(57) ABSTRACT

A method and kit for assaying a cell sample for the presence of at least a threshold number of cells of a given type are disclosed. The kit includes an assay device having a sample chamber for receiving the cell sample and an elongate collection chamber containing a selected-density and/or viscosity medium and having along its length, a plurality of cell-collection regions, and particles which are capable of specific attachment to cells of the selected cell type, and which are effective, when attached to the cells, to increase the density or magnetic susceptibility of the cells. In operation, particle-bound cells and particles in the cell sample are drawn through the elongate collection chamber under the influence of a gravitational or selected centrifugal or magnetic-field force until the particle-bound cells and particles completely fill successive cell-collection regions in the collection chamber. Indicia associated with at least one collection regions indicates a concentration of cells of the selected type effective to at least partially fill that collection region.

2 Claims, 11 Drawing Sheets

U.S. PATENT DOCUMENTS

| | | | |
|---|---|---|---|
| 4,156,570 A | 5/1979 | Wardlaw | |
| 4,190,328 A | 2/1980 | Levine et al. | |
| 4,209,226 A | 6/1980 | Wardlaw et al. | |
| 4,259,012 A | 3/1981 | Wardlaw | |
| 4,558,947 A | 12/1985 | Wardlaw | |
| 5,132,087 A | 7/1992 | Manion et al. | |
| 5,646,004 A * | 7/1997 | Van Vlasselaer | 435/7.25 |
| 5,663,051 A | 9/1997 | Vlasselaer | |
| 5,674,699 A | 10/1997 | Saunders et al. | |
| 5,723,285 A | 3/1998 | Levine et al. | |
| 5,830,639 A | 11/1998 | Levine et al. | |
| 5,834,217 A * | 11/1998 | Levine et al. | 435/7.24 |
| 5,876,593 A | 3/1999 | Liberti et al. | |
| 6,013,532 A * | 1/2000 | Liberti et al. | 436/526 |
| 6,143,577 A | 11/2000 | Bisconte Sconte De Saint Julien | |
| 6,280,622 B1 * | 8/2001 | Goodrich et al. | 210/252 |
| 6,623,983 B1 | 9/2003 | Terstappen et al. | |
| 6,670,197 B2 | 12/2003 | Rimm et al. | |
| 6,790,366 B2 | 9/2004 | Terstappen et al. | |
| 6,821,790 B2 | 11/2004 | Mahant et al. | |
| 6,893,881 B1 | 5/2005 | Fodstad et al. | |
| 6,933,109 B2 | 8/2005 | Anderson | |
| 6,974,701 B2 | 12/2005 | Bouboulis | |
| 6,979,534 B1 | 12/2005 | Siegel | |
| 7,169,578 B2 | 1/2007 | Wang et al. | |
| 7,175,992 B2 | 2/2007 | Fong | |
| 7,651,838 B2 | 1/2010 | Paterlini-Brechot | |
| 2007/0172899 A1 | 7/2007 | Graham et al. | |
| 2010/0068754 A1 | 3/2010 | Kirakossian | |

OTHER PUBLICATIONS

International Search Report for PCT application PCT/US2008/085737, Search Report dated Oct. 15, 2009, 5 pages.

* cited by examiner

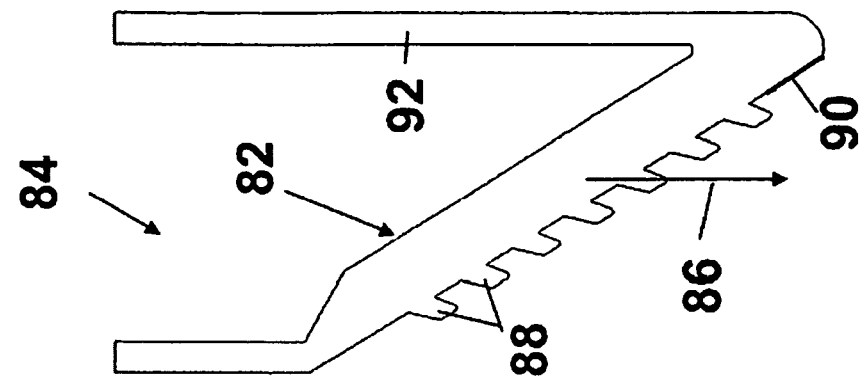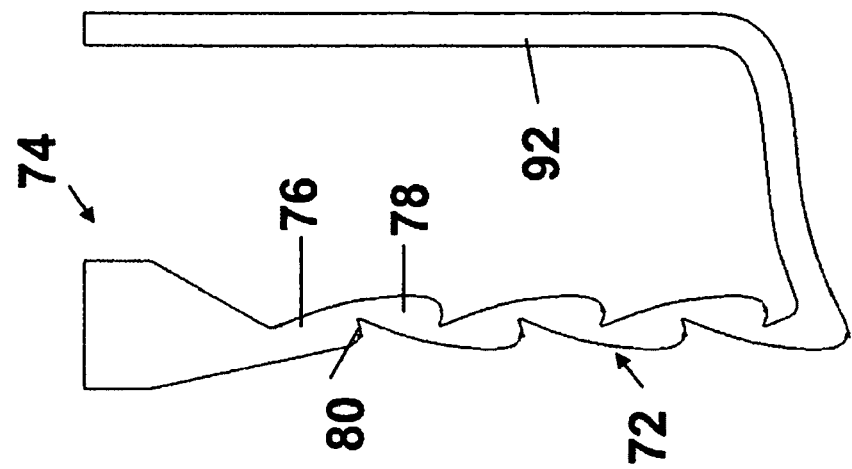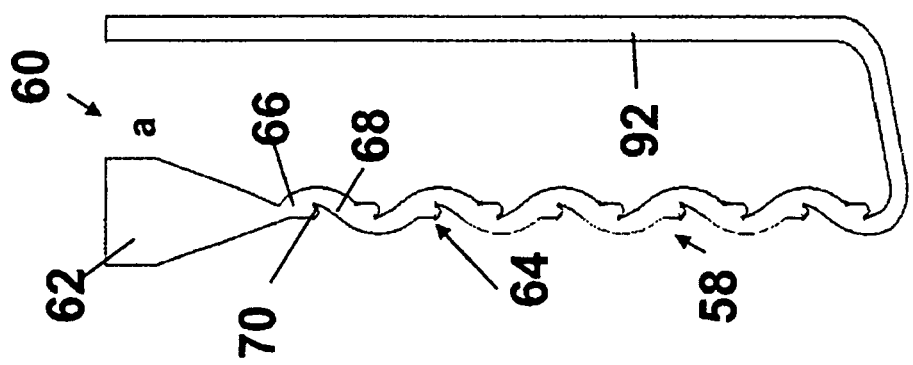

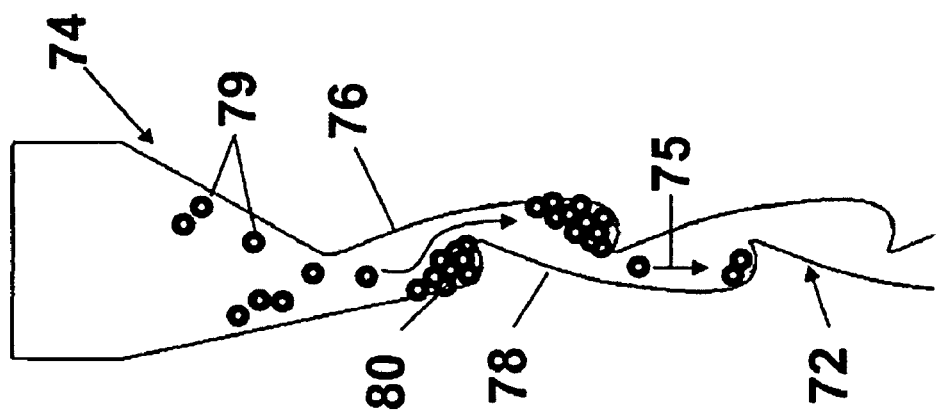

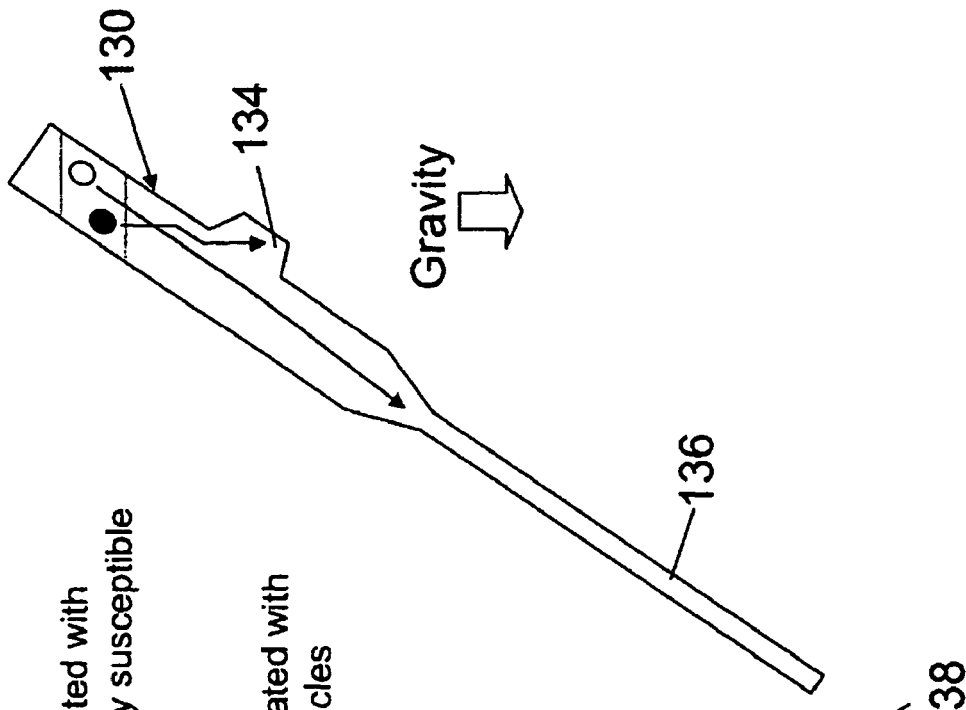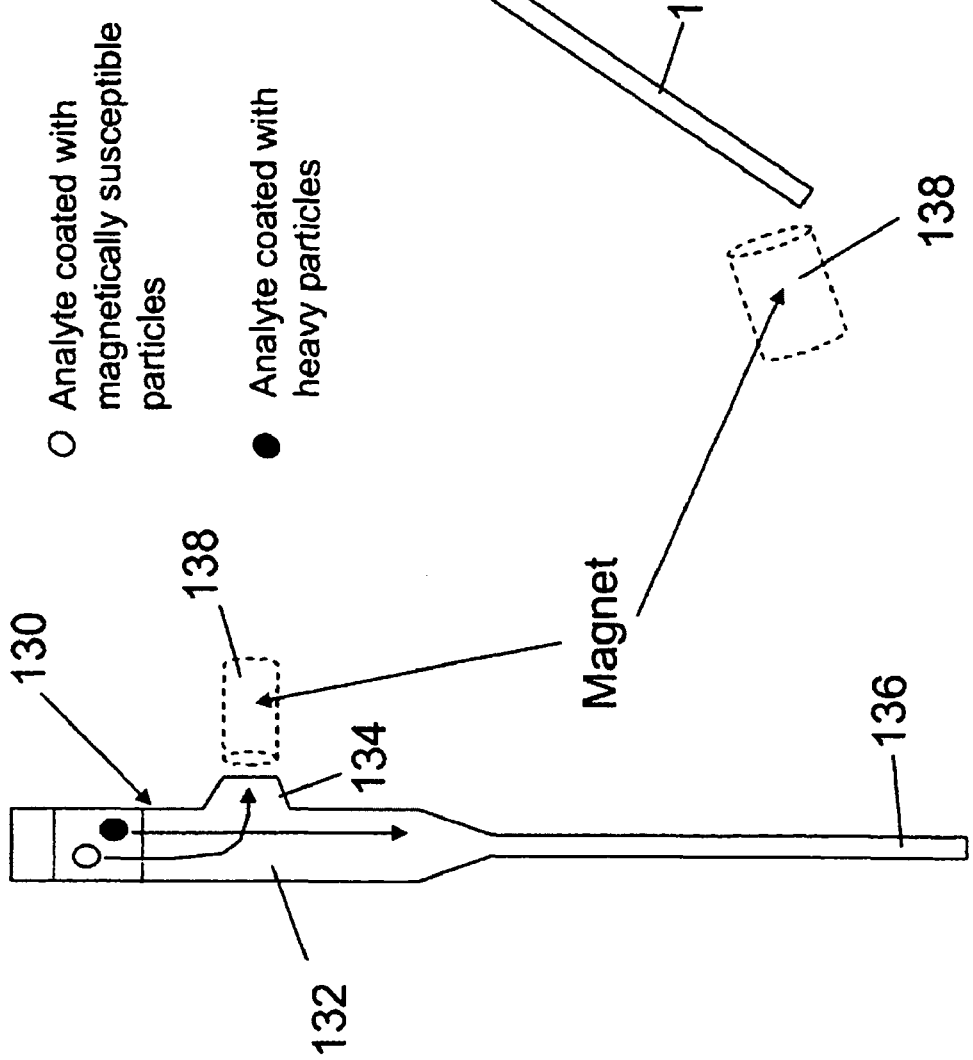

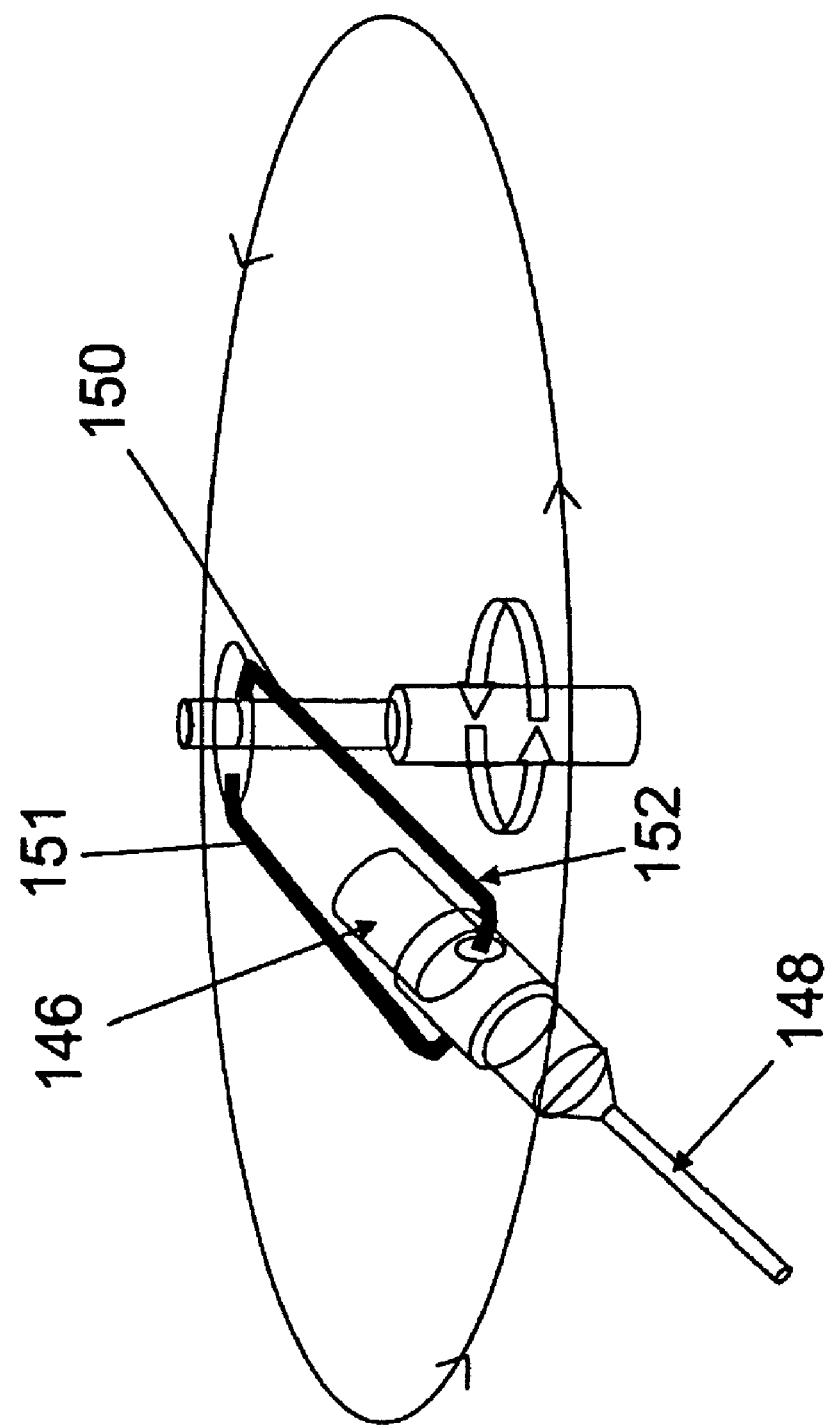

CELL ASSAY KIT AND METHOD

This application claims priority to U.S. Provisional Patent Application No. 60/992,624 filed on Dec. 5, 2007, which is incorporated in its entirety herein by reference.

FIELD OF THE INVENTION

The present invention is directed to a cell assay kit and method for determining the presence and/or concentration of cells of a given type in a cell sample, and in particular, the presence of at least a selected threshold level of the cells in the sample.

BACKGROUND OF THE INVENTION

A variety of disease conditions, including the response to treatment of a disease state, can be monitored by hematology markers, using the approximate concentration of certain white blood cells in a blood sample as an indicator of the body's response to the disease. For example, the concentration of CD4+ T-lymphocyte cells in a blood sample may provide a marker for the outbreak of AIDS following HIV infection. A cell count of lower than about 200 cells/µl blood indicating a seriously weakened immune system and thus the need to immediately start with e.g. antiretroviral treatment (ART). Some disease conditions, such as viral or bacterial infection, are characterized by an increased concentration of blood leukocytes, e.g., above about 10,000 cells/µl blood, which can thus serve as an indicator of an infectious disease state. Conversely, the concentration of leukocytes in a blood sample may be depressed, e.g., below about 4,000 cells/µl blood, in an individual who has leukemia or who is undergoing chemotherapy or radiation therapy. In these and other disease conditions which are characterized by depressed or elevated levels of a white blood cell type, the level of the marker cells can be used to detect or confirm a disease condition, or monitor the body's response to treatment of the condition.

Currently, there are two general hematological methods that are commonly employed for determining the concentration of given cell in a cell sample. In a first approach, the cell type of interest is labeled with a marker that binds specifically to that cell type, typically an antigen-specific antibody. The cell sample is then analyzed with a cell counter, e.g., a flow cytometer or a Fluorescence Activated Cell Sorter (FACS) to determine the percentage of to cells having the surface-bound marker.

The second general approach is to label cells of interest and examine a representative cell volume by microscopic examination, counting the number of labeled and unlabelled cells to determine a percentage of the cell type of interest.

In both approaches, particularly where it is desired to determine the concentration of a given white cell type, the cell sample may first be treated to remove red blood cells or other unwanted cells.

The methods outlined above are well suited to laboratory or clinic settings where there well-trained laboratory personnel and cell-sorting or histology equipment is available. However, they do not lend themselves readily to field settings, such as storefront clinics, or field clinics in third-world countries, where neither trained laboratory personnel or sophisticated cell sorting or microscope equipment are present. In poorer areas of Africa, for example, these methods may be ill suited for testing large numbers of people for CD4+ T cell counts, as an indication of the onset of AIDS following HIV infection, or for monitoring a person's response to e.g. antiretroviral drugs.

It would thus be desirable to provide simple, rapid, inexpensive kit and method for determining cell counts on disease-related cells, e.g., selected white cells in a blood sample. In particular, such a method and kit should be easily executable with only minimal training, and require little or no special lab equipment, e.g., beyond a simple, e.g. manually driven table-top centrifuge.

SUMMARY OF THE INVENTION

The invention includes, in one aspect, a method for assaying a cell sample for the presence of at least a threshold concentration of cells of a given type. The method includes the steps of:

(a) reacting a cell sample containing cells of the given cell type with particles capable of specific attachment to the cells, and being effective, when attached to the cells, to increase the density or magnetic susceptibility of the cells, allowing particle-bound cells and free particles to be separated from non-particle bound cells in the sample based on their greater rate of migration through a selected-density and/or selected viscosity medium under the influence of a gravitational or applied centrifugal or magnetic-field force, (b) causing the particle-bound cells and particles in the cell sample to migrate through an elongate collection chamber containing the selected-density medium and having along its length, a plurality of cell-collection regions, by subjecting the sample to a gravitational or selected centrifugal or magnetic-field force for a period of time sufficient to cause the particle-bound cells and particles to completely fill successive cell-collection regions in the collection chamber, and (c) inspecting the chamber to determine whether the at least one selected collection region is partially or completely filled, as evidence that the cell sample contains at least a threshold concentration of cells of the given cell type.

In one general embodiment, the collection chamber includes a collection column, the collection regions within the column include defined-length segments along a section of the column, and the collection regions are successively filled in step (b) in a downstream-to-upstream direction along the collection chamber's column length.

In another general embodiment, the collection chamber includes an elongate collection tube and, forming the collection regions within the collection tube, a plurality of cavities arranged within the tube such that cells migrating through the tube in an upstream-to-downstream direction in step (b) are trapped in the most upstream cavity until filled, after which the cavities fill successively in an upstream-to-downstream direction.

The particles, when attached to the cells in step (a), may be effective to label the cells with a detectable reporter, and said inspecting includes visually inspecting the collection chamber for the presence of cells labeled with the detectable reporter.

Step (b) in the method may include subjecting the particle-bound cells to gravitational force by placing the chamber in a substantially upright, vertically disposed position, or subjecting the particle-bound cells to a centrifugal force. In these embodiments, the selected-density medium has a density greater than that of the sample and less than that of the particles, and the particles may be substantially spherical metal particles having preferred diameters in a selected size range between about 0.05 to 5 microns, preferably in the 0.2 to 5 micron range.

Alternatively, step (b) in the method may include subjecting the particle-bound cells to magnetic-field force. In this embodiment, the selected-density medium has a density greater than that of the sample, and the particles may be substantially spherical magnetic (ferromagnetic or paramagnetic) particles preferred having diameters between about 5-10'000 nm, preferably in the 5-50 nm range.

Step (b) in the method may further include adding the sample containing particle bound cells to an interface zone upstream of the collection chamber, and physically mixing cells in the sample with a selected-density medium in the interface zone.

Where the cell sample is a blood sample, the particles may have surface bound binding protein capable of immunoreacting with a blood-cell specific antigen, i.e., with an antigen characteristic of a specific cell type or types. The particles may surface treated to reduce particle aggregation in a blood sample.

For detecting the concentration of CD4+ T-lymphocyte cells in a blood sample from an individual who may be infected with HIV, as an indicator of the T-cell category of the individual, reacting step (a) may be carried out by exposing a blood-fluid sample from the individual to particles having surface-bound anti-CD4+ binding agent, and step (c) may be based on observing the presence of cells in a collection region that indicates a concentration of CD4+ T-lymphocyte cells in a selected threshold range of between 200-750 cells/µl blood, e.g., a threshold of 250, 350, 450, or 750 cells/µl blood.

In one embodiment, step (a) may further include reacting cells in the sample with first particles capable of binding specifically to CD14 antigen on monocyte cells, and with second particles capable of binding specifically CD4 antigen on T lymphocyte cells and monocyte cells, thus to confer on the T lymphocyte cells, enhanced density, and on the monocyte cells, both enhanced density and magnetic susceptibility, and step (b) may further include first removing particle-bound monocytes from the cell sample by application of a magnetic force effective to selectively remove the particle-bound monocytes from particle-bound T lymphocyte cells. Both particles may also be applied simultaneously in defined ratios, ensuring that statistically the monocyte cells are bound to at least one particle having magnetic susceptibility. Other possible approaches to remove non-desired cells having the same surface marker as the target cells are: i) Masking of the target surface markers with sterically large beads having an affinity for other, non-target surface markers on the interfering cell types (e.g. using non-dense and non-magnetically susceptible anti-CD14 beads to first coat the monocytes before exposing the sample to the anti-CD4 beads), thus preventing the anti CD4 beads to bind to the CD4 markers on the monocytes due to the masking effect of the antiCD14 beads covering the monocytes. ii) Masking the target surface markers on non desired cells by other means like using antibody mediated tetrameric antibody complexes which have specificity to both, e.g. CD14 antigen and red blood cell surface markers, thus masking the monocytes by covering them with a dense layer of red blood cells. iii) The interfering non-target cells can be removed by specifically capturing these cells by a solid matrix containing e.g. antibodies against surface markers only present on the interfering cells. For example, antiCD14 antibody can be immobilized on a filter matrix. After exposing the blood sample to that filter matrix, the monocytes are depleted from the blood sample by binding to that matrix, after which the blood sample is exposed to the antiCD4 particles.

For detecting the concentration of leukocytes in a blood sample from an individual who may have an infection or other condition leading to an elevation of leukocytes in the blood, reacting step (a) may be carried out by exposing a blood-fluid sample from the individual to particles having surface-bound anti-leukocyte binding agent, and step (c) may be based on observing the presence of cells in a collection region that indicates a concentration of leukocytes of greater than about 10,000 cells/µl blood.

For monitoring the concentration of leukocytes in a blood sample from an individual who may have depressed numbers of leukocytes in the blood, due to chemotherapy, radiation therapy or leukemia, reacting step (a) may be carried out by exposing a blood-fluid sample from the individual to particles having surface-bound anti-leukocyte binding agent, and step (c) may be based on observing the presence of cells in a collection region that indicates a concentration of leukocytes of less than about 4,000 cells/µl blood.

For monitoring the concentration of neutrophils in a blood sample from an individual who may depressed numbers of neutrophils in the blood, due to chemotherapy or interferon therapy, reacting step (a) may be carried out by exposing a blood-fluid sample from the individual to particles having surface-bound anti-neutraphile binding agent, and step (c) may be based on observing the presence of cells in a collection region that indicates a concentration of neutrophils in a selected range between 500 and 2,500 cells/µl blood, e.g., 500, 2,000 or 2,500 cells/µl blood.

For detecting the concentration of bacterial cells in a blood sample from an infected individual, as an indicator of the extent and type of infection, reacting step (a) may be carried out by exposing a blood-fluid or urine sample from the individual to particles having a surface-bound binding agent capable of binding specifically to one or more selected bacterial-wall antigens, and step (d) may be based on observing the presence of cells in a collection region that corresponds to a detectable concentration of bacterial cells in the blood sample.

In another aspect, the invention includes a kit for assaying a cell sample for the presence in the sample of at least a threshold concentration of cells of a selected cell type. The kit comprises:

(a) an assay device having a sample chamber for receiving the cell sample and, in fluid communication therewith, an elongate collection chamber containing a selected medium and having along its length, a plurality of cell-collection regions, (b) particles which, when added to the cell sample, are capable of specific attachment to cells of the selected cell type, and which are effective, when attached to the cells, to increase the density or magnetic susceptibility of the cells, allowing particle-bound cells and particles in the cell sample to migrate preferentially through the elongate collection chamber under the influence of a gravitational or selected centrifugal or magnetic-field force until the particle-bound cells and particles completely fill successive cell-collection regions in the collection chamber, and (c) an indicium or indicia associated with at least one collection regions on the device collection chamber indicating the concentration of cells of the selected type effective to at least partially fill that collection region, when particle-bound cells and free particles are drawn through the collection chamber.

In various embodiments: (1) the collection chamber includes a collection column, the collection regions within the column include defined-length segments along a section of the column, and the collection regions are adapted to be successively filled in step in a downstream-to-upstream direction along the collection chamber's column length; (2) the collection chamber includes an elongate collection tube and, forming the collection regions within the collection tube, a plurality of cavities arranged within the tube along its length, and the collection regions are adapted to be successively filled in an upstream-to-downstream direction along the column length; (3) the collection chamber includes a collection tube having a plurality of oppositely angled flow segments and, forming the collection regions within the collection tube, a plurality of rimmed cavities disposed between adjacent flow segments, such that cells migrating from one flow segment to another, in an upstream-to-downstream direction, are trapped in the cavity between the two flow segments until that cavity is filled; (4) the collection chamber includes a collection tube that is angled with respect to the direction of flow of particle-attached cells within the tube under a gravitational force and, forming the collection regions within the collection tube, a plurality of cavities disposed along an outer surface portion of the tube, such that cells migrating through the collection tube, in an upstream-to-downstream direction, are trapped in the most upstream cavity until filled; and (5) the collection chamber includes a flow tube extending substantially transversely with respect to the direction of flow of particle-attached cells under a gravitational force and, forming the collection regions within the collection chamber, a plurality of cavities disposed along a length of the flow tube, such that cells flowing through the flow tube, in an upstream-to-downstream direction, sediment into the most upstream cavity until filled, after which the cavities fill successively in an upstream-to-downstream direction.

The device may further include a catch chamber communicating with the sample chamber, and particles (b) may include a first type of particles capable of binding specifically to an antigen present on cells of the selected type and on a cells of a non-selected type, and a second type of particles capable of binding specifically to an antigen present on cells of the non-selected type only, allowing particles bound to second type of particles to be selectively removed by migration into the catch chamber, before migration of the cells of the selected type, which are bound to the first type of particle only, to migrate selectively through the collection chamber.

Where the particle-bound cells are adapted to migrate through the collection zone under the influence of a gravitational or applied centrifugal force, the particles may be substantially spherical metal particles having diameters in a preferred selected size range between about 0.2 to 2 microns. For detecting cells of a given type in a blood sample, the particles may have surface bound binding protein capable of immunoreacting with a blood-cell specific antigen. The particles may be surface treated to reduce particle aggregation in a blood sample, e.g., coated with a hydrophilic polymer coating such as polyethylene glycol polymer chains.

Where the particle-bound cells are adapted to migrate through the collection zone under the influence of a magnetic-field force, the particles may be substantially spherical magnetic particles having diameters in a preferred selected size range between about 5-50 nm.

For detecting the concentration of CD4+ T-lymphocyte cells in a blood sample from an individual who may be infected with HIV, as an indicator of the T-cell category of the individual, the particles may have surface-bound anti-CD4 binding agent, and the indicia may be designed to indicate a concentration of CD4+T-lymphocyte cells of about 200 cells/µl blood and/or a concentration of cells of about 500 cells/µl blood.

For detecting the concentration of leukocytes in a blood sample from an individual who may have an infection or other condition leading to an elevation of leukocytes in the blood, the particles may have surface-bound anti-leukocyte binding agent, and the indicia may be designed to indicate a concentration of leukocytes of greater than about 10,000 cells/µl blood.

For monitoring the concentration of leukocytes in a blood sample from an individual who may depressed numbers of leukocytes in the blood, due to chemotherapy, radiation therapy or leukemia, the particles may have surface-bound anti-leukocyte binding agent, and the indicia may be designed to indicate a concentration of leukocytes of less than about 4,000 cells/µl blood.

For detecting the concentration of neutrophils in a blood sample from an individual who may have depressed numbers of neutrophils in the blood, due to chemotherapy or interferon therapy, the particles may have surface-bound anti-neutraphile binding agent, such as CD16, and the indicia may be designed to indicate a concentration of neutrophils in a selected range between 500 and 2,500 cells/µl blood.

For detecting the presence of a bacterial infection in a blood or urine sample from an infected individual, the particles may have surface-bound binding agent capable of binding specifically to a bacterial-wall antigen, and the indicia may be designed to indicate the presence of cells in the blood or urine sample.

The kit may further include a device holder for holding the device and for applying to the held device, a centrifugal or magnetic-field force.

These and other and features of the invention will become more fully apparent when the following detailed description of the invention is read in conjunction with the accompanying drawings.

BRIEF DESCRIPTION OF THE DRAWINGS

FIGS. 3A-3C show side sectional views of the collection chambers in a second general embodiment of the device of the invention, in which the collection chamber includes a plurality of angled flow segments and rimmed cavities disposed between adjacent flow segments (FIGS. 3A and 3B) and in which the collection chamber is angled with respect to the direction of flow of particle-attached cells within the tube under an applied force, and having a plurality of cavities disposed along an outer surface portion of the tube (FIG. 3C);

FIG. 4 illustrates the accumulation of particle-attached cells in cavities in the devices illustrated in FIG. 3B, successively in an upstream-to-downstream direction;

FIGS. 9A and 9B illustrate an assay using a two-chamber device that allows for initial removal of an unwanted cell type that shares a critical surface-antigen with the cell type of interest; and FIGS. 10A-10C illustrate a sample device in a holder suitable for cell migration by sedimentation (10A), or under an applied centrifugation (10B) or magnetic-field (10C) force

DETAILED DESCRIPTION OF THE INVENTION

I. Definitions

Figure 2:
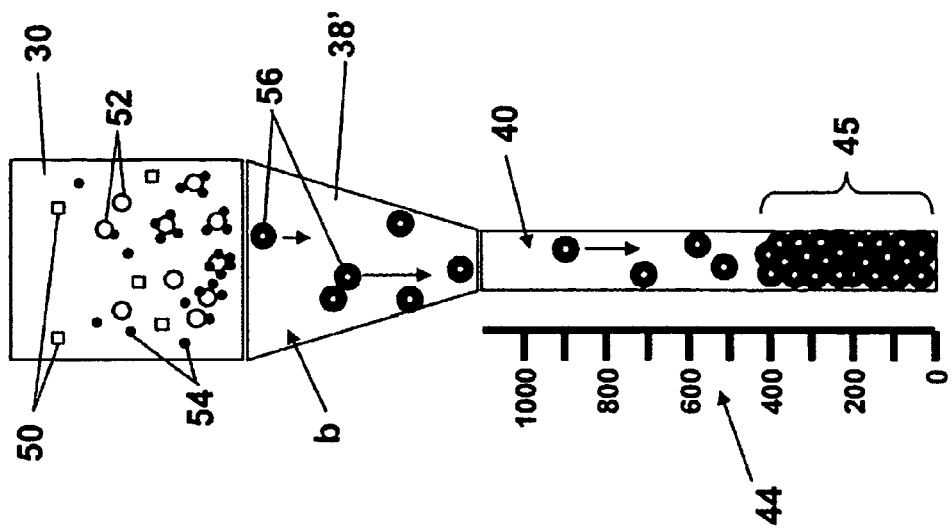
FIG. 2 illustrates binding and cell-migration events underlying the operation of the assay kit of the invention, in one general embodiment.

Unless otherwise, the terms below have the following meaning herein:

A "cell sample" refers to any liquid sample containing or suspected of containing one or more types of cells in suspension. A cell sample includes a "body-fluid sample," referring to e.g. a blood, urine, or saliva sample obtained from a human or other animal body. A blood sample may be whole blood or processed blood or whole blood in which all or the bulk of red blood cells have been removed. Other possible cell samples include e.g. cell cultures, cell extracts obtained from tissue samples, waste-water. Cell samples that are suspected of containing cells include e.g. milk and other food that is contaminated with an unwanted e.g. cell or bacteria type.

"Concentration" of cells in a cell sample refers to the number of cells in a given cell-sample volume. The term is typically expressed as number of cells/per sample volume.

A "threshold level or concentration of cells of a given type" refers to a threshold number of the cells contained in a given volume of sample, also expressed as a cell concentration, such as a number of CD4+ cells greater than 500 cells/µl of blood sample, or number of CD4+ cells less than 200 cell/µl blood sample.

"Sedimentation" of cells refers to particles in a liquid suspension settling out of the suspension, or toward the bottom of the suspension or into another liquid medium of different density or viscosity, under the influence of a gravitational force.

Cells of a given type" or "analyte" cells refer cells whose concentration in a sample are to be assayed. The cells may be bacterial or viral particles, e.g., from a body-fluid sample, mammalian cells, such as the white blood-cell types listed in the table below or cell fragments such as platelets, from a blood sample, tissue- or organ-derived mammalian cells, such as cancer cells derived from a solid tumor or other tissue mass, cultured or other dissociated plant or animal cells, cells from single-cell eukaryotes, such as yeast cells, and cells contained in an industrial, environmental or urban samples, e.g. bacteria contained in soil or wastewater samples. A given type of white cell can typically be characterized by cell-surface specific antigen markers, such as CD the CD antigen markers characteristic of white cell types indicated in the table below.

| Type of cell | CD markers |
| --- | --- |
| stem cells | CD34+, CD31− |
| all leukocyte groups | CD45+ |
| Granulocyte | CD45+, CD15+ |
| Monocyte | CD45+, CD14+ |
| T lymphocyte | CD45+, CD3+ |
| T helper cell | CD45+, CD3+, CD4+ |
| Cytotoxic T cell | CD45+, CD3+, CD8+ |
| B lymphocyte | CD45+, CD19+ or CD45+, CD20+ |
| Thrombocyte | CD45+, CD61+ |
| Natural killer cell | CD16+, CD56+, CD3− |

"Migration" of cells refers to the movement of cells through a medium, typically having a selected density, under the influence of a gravitational force, or an applied centrifugal or magnetic-field force.

Particles, such as metal particles, are effective to increase the density of cells to which the particles are attached. The cells and attached particles have a combined greater density than the cells alone, as evidence, for example, by the greater migration rate of the cells and attached particles through a given-density medium, under the influence of a gravitational or applied centrifugal force.

Magnetic particles, including either ferromagnetic and paramagnetic particles, are effective to increase the magnetic susceptibility of cells to which the particles are attached if the cells and attached particles have a combined magnetic susceptibility greater than the cells alone, as evidence, for example, by the greater migration rate of the cells and attached particles through a given-density and/or viscosity medium, under the influence of an applied magnetic field.

"Magnetic susceptibility" is a measure of the intensity of magnetization of a body placed in a uniform magnetic field.

"Microchannel" or microscale channel or column" refers to a channel or column having dimensions in the micro-scale range, typically between 10-500, e.g., 50-100 microns in width and depth.

II. Assay Device and Kit

Figure 1:
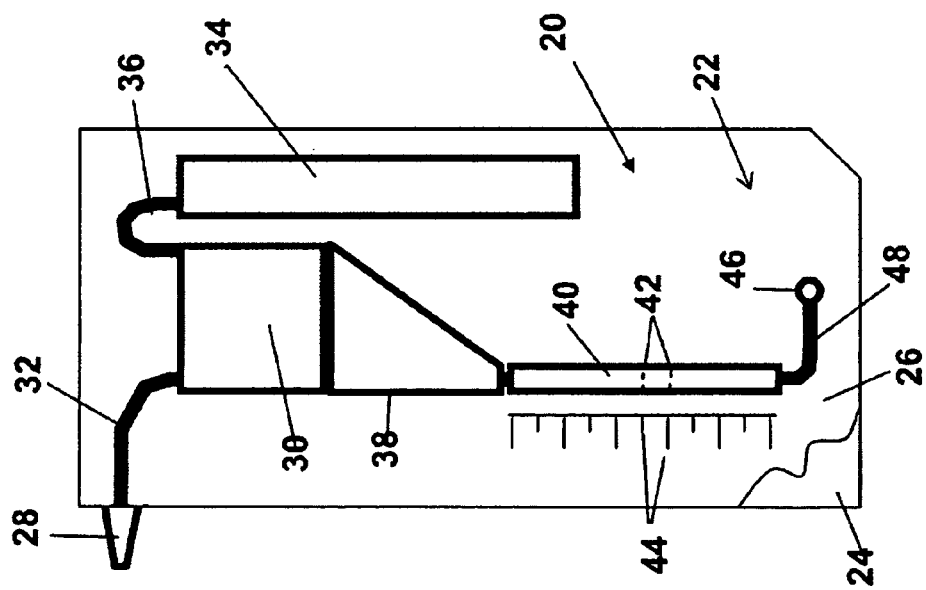
FIG. 1 is a plan view of an assay device forming part of the kit of the invention, in one general embodiment.

FIG. 1 shows a cell assay kit 20 constructed according to one embodiment of the invention. The device includes a substrate or backing 22 on which other components of the device are mounted or incorporated into. For example, certain reservoir and channel components described below maybe incorporated into the substrate as microfluidics components formed according to well known methods between two substrate plates, e.g., where the reservoir and channel components are formed as recesses in a lower plate 24 which is covered by an upper cover plate 26. In a preferred embodiment, the chambers and connecting micro-channels of the device are constructed of a smooth-surface material, like glass or hard polymer material, and the chamber and channel surfaces are coated with a coating to minimize non-specific attachment of cells to the channel walls. For example, the channel walls can be coated by pegylated, polyionic copolymers as described in U.S. Pat. Nos. 5,567,440, 6,884,628 and 5,462,990. Other coatings known in the art to reduce or prevent the non-specific or non-desired sticking of cells to the channel walls such as coatings based on specific silanes, alkanethiol-self-assembled monolayers, PEG copolymers, surfactants and inorganic layers or passively adsorbed proteins like e.g. BSA or blood sera may be employed.

As seen in the figures, the device includes a sampling head 28 designed to take up a cell sample, e.g., by capillarity, by immersing the head in the sample. The sample head may be a finger-prick needle or other capillary structure for drawing a fixed volume of sample. The head is connected to a sample chamber 30 through a microchannel tube 32. The sample chamber may be pre-filled with given volume of a suspension of particles (i) capable of specific attachment to the given type of cell to be assayed (ii) when attached to the cells, substantially increasing the density or magnetic susceptibility of the cells, i.e., impart a substantially higher density or magnetic susceptibility to the cells to which the particles bind. Particles suitable for use in the invention will be described below with reference to FIG. 2. The device shown in FIG. 1 and the particles contained in or added to the sample chamber with the sample, is also referred to herein, collectively, as an assay kit.

An overflow reservoir 34 in the device is connected to sample chamber 30 through a microchannel tube 36, and functions to receive overflow liquid as a given volume of sample is added to the device. The sample chamber communicates along its lower end with an interface chamber 38. As seen, chamber 38 in FIG. 1 is tapered in a downward direction from one side only; an equivalent-function interface chamber 38' in FIG. 2 is tapered symmetrically from both sides of the sample chamber; and in FIG. 6, an interface zone is formed as separate chambers 38", 39", respectively.

The lower end of chamber 38 in FIG. 1 (or chamber 38' in FIG. 2 or chamber 39" in FIG. 6) is in fluid communication with an elongate collection chamber 40. In the general embodiment shown in FIGS. 1, 2, and 6, the collection chamber is an elongate microchannel having defined-length segments along a length of the column, such as the segment 42 defined by a pair of markers, or indicia, such as markers 44 displayed along a length of the column. As seen in FIG. 2, these column segments or regions, which are indicated by the displayed indicia, are used to determine the number of cells, or cell count of the sample, as determined by height of the top of the plug of cells that have migrated into the column. Thus the indicia displayed along the length of the column provide a readout of the assay results. Although not shown here, the device may be provided with a lens element placed in front of the collection chamber for enhancing the detection of cells within the cell region. Detection of cell levels in the within the collection chamber by spectroscopic or electronic monitoring, according to known methods, is also contemplated, although one advantage of the embodiment illustrated is that the assay read out may be determined by simple visual inspection of the distribution of cells within the collection chamber.

As will be appreciated from the described assay procedures below, the total volume of cells collected in the collection chamber will reflect the combined volume of both cells with bound particles and free particles. In the case of larger particles, e.g., in the 0.5 to 5 micron size range, the particles may make a measurable contribution to the total volume of cells in the collection chamber. In this case, the volume contribution of the particles may be compensated for by providing in the reservoir segments, a "null" segment corresponding to the volume of the added particles alone. In this configuration, the total volume of cells with bound particles plus any free particles will be assumed to be equal to the total volume of free particles plus the total volume of native cells without bound particles. Where the particles are quite small, e.g., for small magnetic particles, the volume contribution of the particles may be negligible, in which case there may be no need to adjust the reservoir volumes for particle-volume effects. However, even in the case of relatively small particles, if a large number excess of particles is added to the cells, e.g., to ensure complete reaction in a sample containing a high concentration of analyte cells, the particles may make a appreciable contribution to the measured stacking or depletion volume, requiring adjustment of the reservoir volumes to compensate for particle volume. The particle-volume effect can be readily determined e.g. by centrifuging the quantity of particles to be added to the sample through the collection chamber, and measuring the volume contribution of the particles alone.

Completing the description of what is shown in FIG. 1, a fill port 46 communicated with the lower end of column 40 through a microchannel 48, allowing the column and interface zone to be filled with a suitable-density medium at the time of manufacture or just prior to an assay. In a general embodiment in which cells migrate through the medium under gravity or an applied centrifugal force, the medium has a specific density less that that particle-attached cells formed in the sample chamber, and preferably equal to or greater than sample cells not attached to the particles.

FIGS. 2 and 3 illustrate the cell reaction and migration events underlying the operation of the device. In FIG. 2, sample chamber 30 is filled with a given, preexisting suspension of reaction particles or beads and receives a defined volume of sample to fill the chamber, or receives a defined combined volume of sample pre-mixed and pre-reacted with a given volume of particle suspension. Where the cells are allowed to migrate into and through the collection chamber under a gravitational or applied centrifugal force, the particles added to the sample cells are relatively high in density, typically greater than about 5 gm/cc, and are formed by metal, ceramic material, high-density glass, and the like. The particles are coated, e.g., by covalent attachment, with a binding agent capable of specific high-affinity binding to a cell-surface antigen unique to the cells of interest in the assay. Thus, for example, in an assay for CD4+ cells, the particles may be coated with antibodies, e.g., monoclonal antibodies, specific to the CD4+ antigen.

A variety of cell-antigen-specific antibodies are commercially available or readily obtainable by known monoclonal antibody methods. One exemplary particle is a 1 micron gold micro-particle having monoclonal antibodies attached via amine or carboxyl chemical groups on the particle surfaces, and having a density of close to that of gold, about 19.3 grams/cc. Other particles include micron-sized or colloidal particles of other metals, oxides or polymers (e.g. iron, silver, glass, silicon or PTFE micro or nano particles), as well as silver or gold SERS (surface-enhanced Raman spectroscopy) particles, polymer-coated metal particles, and quantum dots. The particles are also preferably effective to label the cells with a detectable reporter. The reporter may be the particle itself, such as gold particles that can be easily visualized in concentrated form, or may be an added label, such as a fluorescent label attached to the particles directly or to the binding agent coating the particles. Magnetic or paramagnetic particles suitable for use in biological application, and having surface chemical groups suitable for addition of cell-specific binding agents are well known, and readily available, e.g., from invitrogen (Carlsbad, Calif.).

The particles may additionally be surface treated or coated to reduce the tendency of the particles to self-aggregate in suspension. In one exemplary method, the particles are coated with a hydrophilic polymer, preferably one that is highly solvated in an aqueous medium, such as polyethylene glycol polymer chains. Methods for preparing particles with surface-reactive groups, such as alcohol, acid, or amine groups, attaching polymer chains to such groups are known.

In FIG. 2, non-analyte cells, such as cells 50 are indicated by open squares, analyte cells, such as cells 52, by open circles, cell-binding particles, such as particles 54, by solid circles, and particle-bound cells, such as cell 56 by darkened open circles. Initially, the sample and particles may be pre-mixed and reacted in a separate tube, then added together to the sample chamber, allowing the reacted cells to sediment from the sample chamber through the sedimentation zone into the collection chamber. Alternatively, the sample may be added directly to the sample chamber for reaction with particles in the chamber, in which case the device may be placed in a horizontal position to prevent particles and cells from sedimenting toward the collection column before the cell-binding reaction is complete.

Figure 10A:
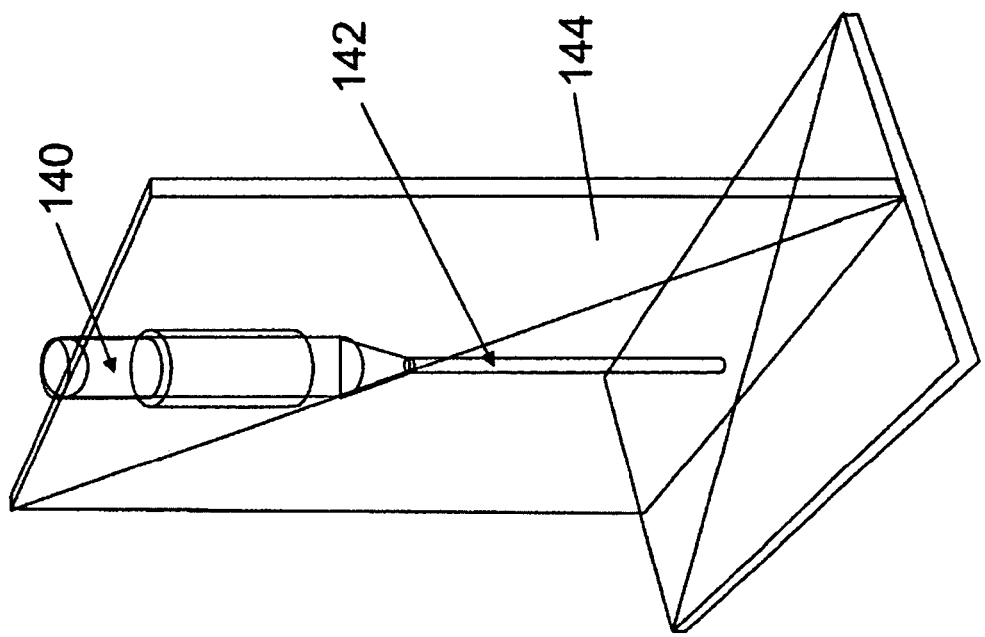
Figure 10C:
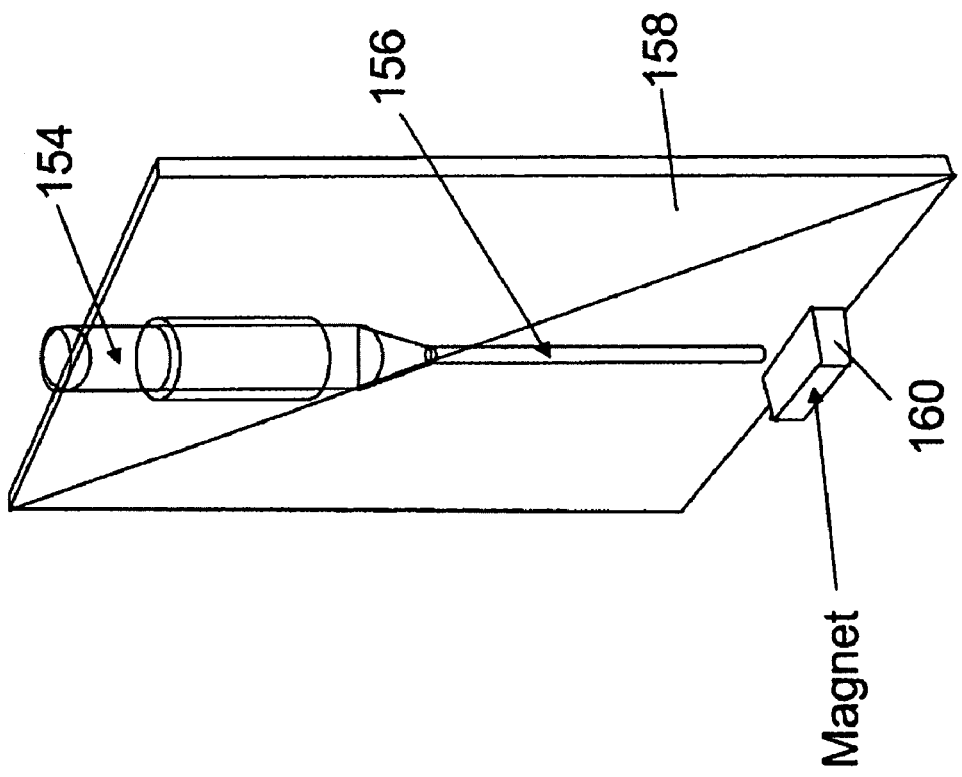

After a suitable reaction time, e.g., 10 minutes, the device is placed in a suitable holder for promoting migration of the cells with bound particles to migrate into the collection chamber, as illustrated in FIGS. 10A-10C. Where particle migration through the collection zone is by sedimentation under gravity, the holder simply acts to place the collection chamber is an upright, and preferably vertically upright position, as shown in FIG. 10A, where assay device 140 having a collection chamber 140 is placed in a table-top holder 144 adapted to support the device in a substantially vertical, upright position. Where particle migration is by centrifugation, the holder may be simply a tube holder that is adapted for placing in the head of a centrifuge, e.g., a typical table-top centrifuge tube holder, as illustrated in FIG. 10B. Here assay device 146 having a collection chamber 148 is engaged, e.g., by receiving sockets on opposite side of the device, by the spreadable arms 151 of a U-shaped fork 152 which is carried for rotation on the shaft 150 of a centrifuge, for rotation about the shaft axis. The centrifuge may be, for example, an inexpensive manually driven table-top centrifuge. The centrifuge and attached fork thus serve as the device holder in this embodiment. Where particle migration is by application of a magnetic-field, the holder may simply be a stand having a permanent or electromagnet at its base, as shown in FIG. 1C, which illustrates an assay device 154 having a collection chamber 156 mounted upright in a stand 158. A permanent magnet 160 at the lower end of the stand is used to drawn magnetic-bead-bound cells into and through the collection chamber. In each mode, the assay promotes particle-bound cells (and free particles) to migrate into the through the interface zone (chamber 38') and into column 40, where the cells accumulate to a final depth proportional to the number of particle-bound cells in added sample. The markings displayed along the column are calibrated to indicate the cell number, preferably indicated as a cell concentration, corresponding to a given sample volume. The holder shown in each embodiment may form part of an assay kit, in accordance with the present invention, that also includes the assay device and cell-specific particles reacted with the cell sample.

In another embodiment of the invention, illustrated in FIGS. 9A and 9B, the cell sample contains analyte cells with a given cell-surface marker and unwanted cells having both the analyte-cells marker and a second cell-specific marker. For purposes of illustration, a cell assay for CD4+ T cells in a blood sample will be described. Cells in the sample contain both CD4+ T cells and unwanted monocytes with surface CD4 antigen, while the monocytes additionally contain CD14 surface antigen. The cell sample is reacted with heavy particles coated with antibodies against one of the two antigens, with magnetic beads coated with antibodies against the other of the two cell-surface antigens. The assay device, shown at 130, includes a sample receiving and interface zone (s) 136, a collection chamber 136, and a catch chamber 134 for collecting the unwanted monocytes.

In the assay illustrated in FIG. 9A, the cell sample is reacted with a mixture of heavy particles, e.g., gold particles, that are immunoreactive with CD4 antigen, and therefore will bind to both CD4+ T cells and CD4+ monocytes, and magnetic beads that are immunoreactive with CD14, and therefore will react with the CD4/CD14 monocytes. After a suitable reaction time, the particle-bound cells are allowed to sediment under gravity in the device. As the cells sediment, a magnet 138 applied near the catch chamber draws unwanted monocytes into the catch chamber, freeing the CD4+ T cells sedimenting into the collection chamber of unwanted monocytes.

In the assay illustrated in FIG. 9B, the roles of the two particles are reversed, with the heavy particles being immunoreactive against CD14, and the magnetic beads, immunoreactive against CD14 antigen. After reaction of the cells with the two particle types, the assay device is angled as shown, allowing the monocytes labeled with the heavy particles to sediment into catch chamber 134, removing these cells from the CD4+ T cells, which are drawn into the collection chamber by a magnet 138 at the lower end of the chamber.

FIGS. 3A-3C illustrate the collection chamber configurations in a cell-sedimentation assay device like that described above, but constructed according to a second general embodiment of the invention. In all of these devices, the collection chamber includes an elongate collection tube and, forming the collection regions within the collection tube, a plurality of cavities disposed along the tube. The cavities are arranged within the tube such that cells migrating through the tube in an upstream-to-downstream direction are trapped in the most upstream cavity until filled, after which the cavities fill successively in an upstream-to-downstream direction.

FIG. 3A shows a an assay device 60 having an interface zone 62 communicating with a collection tube or chamber 64. The collection tube has a plurality of oppositely angled flow segments, such as segments 66, 68. The collection regions within the tube are a plurality of rimmed cavities disposed between adjacent flow segments, such as cavity 70 between adjacent flow segments 66, 68.

The collection chamber shown in FIG. 3B is similar to that of FIG. 3A. Here a collection tube 72 in an assay device 74 is formed of oppositely angled flow segments, such as segments 76, 78, and a series of cavities between adjacent flow elements, such as cavity 80 between flow segments 76, 78. A portion of this configuration is shown in FIG. 4, and illustrates how cells migrating through the collection tube are trapped in the cavities successively in an upstream-to-downstream direction, allowing cell count to be readily determined by identifying the most downstream cavity containing particle-attached cells. As seen in FIG. 4, particle-bound cells, such as cells 79, migrating from one flow segment to another, in an upstream-to-downstream direction (top-to-bottom in the figure, along a line of force indicated by arrow 75, are trapped in the upstream most cavity 80 until this cavity is filled, at which point cells will start to fill the next most downstream cavity, and so on, until all of the cells have been captured. The number of cells captured in the collection tube can be determined, semi-quantitatively, by determining the most downstream cavity that contains cells. In an actual assay device, the collection regions are calibrated so that each successive collection zone represents a certain total number of sample cells of interest, e.g., approximately 200 cells/per cavity, such that the presence of cells in the nth cavity from the top indicates a cell count of between about, for example, $(n-1)\times 200$ and $n\times 200$ cells. As described above, the relationship between cavity size and number of cells can be adjusted to correct for particle volume (both bound and free particles) filling the reservoirs.

In FIG. 3C, a collection tube 82 in a device 84 is angled with respect to the direction of flow of particle-attached cells, within the tube under a gravitational or applied centrifugal or magnetic-filed, indicated by arrow 86. The collection regions within the collection tube include a plurality of cavities, such as cavities 88, disposed along an outer surface portion 90 of the tube, such that cells migrating through the collection tube, in an upstream-to-downstream direction, and in a direction of force indicated by arrow 86, are trapped in the most upstream cavity first, and then successively in more downstream cavities as each cavity fills. As with the embodiments illustrated in FIGS. 3A and 3B, the device allows cell count to be readily determined by identifying the most downstream cavity containing particle-attached cells.

Also shown in all three devices is a pre-filling channel 92 communicating with the lower end of the collection tube, providing a port through which the collection tube and interface zone can be filled.

Figure 5:
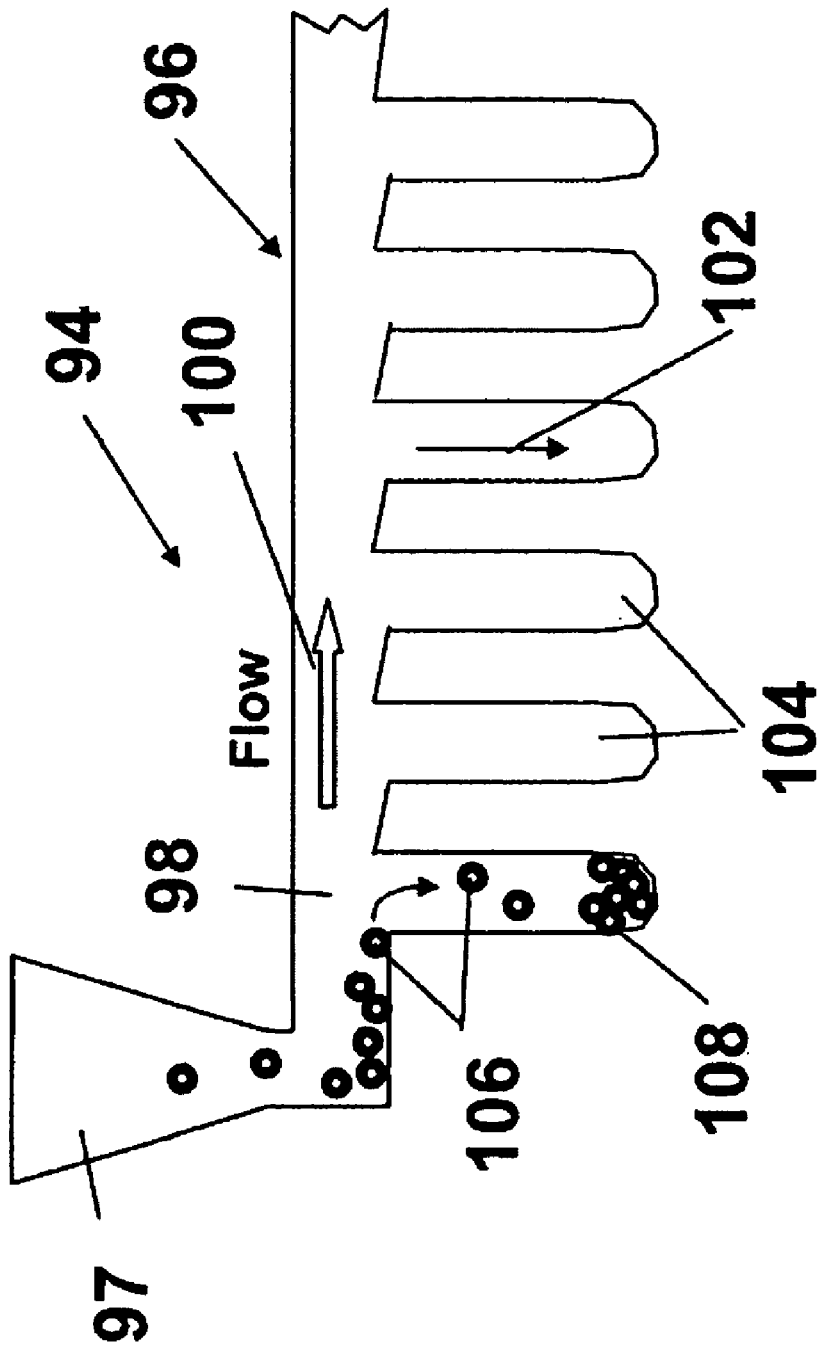
FIG. 5 is a side sectional view of the collection chamber in a third general embodiment of the invention.

FIG. 5 illustrates the collection chamber configuration in a cell-sedimentation assay device 94 like that described above, but constructed according to a third general embodiment of the invention. In this device, the collection chamber, indicated at 96, includes a flow tube 98 communicating at its upstream end with a sedimentation zone 97, and extending substantially transversely with respect to the direction of flow of particle-attached cells under a gravitational force. That is, the direction of flow through tube, indicated by arrow 100, is substantially perpendicular to the direction of force applied to the cells, e.g., under a gravity, indicated by arrow 102. The chamber includes a plurality of cavities 104, spaced along the lower face of tube 98. In operation, particle-attached cells, such as indicated at 106, are flowed through the chamber at a flow rate such that the particles will first migrate substantially exclusively into the most upstream cavity, indicated at 108, and when this cavity is filled, the particles continuing to collect at cavity 108 will be carried with the fluid flow so as to sediment into the next downstream cavity, and likewise into each adjacent cavity until all of the cells have been captured in a cavity. As with the other devices in this general embodiment, the cell count of particle-attached cells can be determined from the most downstream cavity containing cells.

III. Assay Method

The method of the invention uses the above cell-assay device for assaying a cell sample for the presence of at least a threshold concentration of cells of a given type. For purposes of illustration, the method will be illustrated with respect to a method for determining a threshold concentration (cell count) of CD4+ T cells present in an HIV-infected individual being monitored for the status of the infection. In general, a CD4+ cell count of between 500-1500 CD4+ T cells/µl blood indicates normal functioning of T-cell immunity in the individual, where cell migration is produced by sedimentation through a defined-density medium under gravitation force. When HIV kills $CD4^+$ T cells so that there are fewer than 200 $CD4^+$ T cells/µl blood, cellular immunity is lost, leading to a likely diagnosis of AIDS. The assay illustrated here is designed to detect a threshold level of CD4+ T cells less than 250/µl blood, meaning treatment is advised at this threshold. This threshold could be adjusted, e.g., depending on the age of the individual to, to say, 350, 450, 550, or 750/µl blood.

Figure 6:
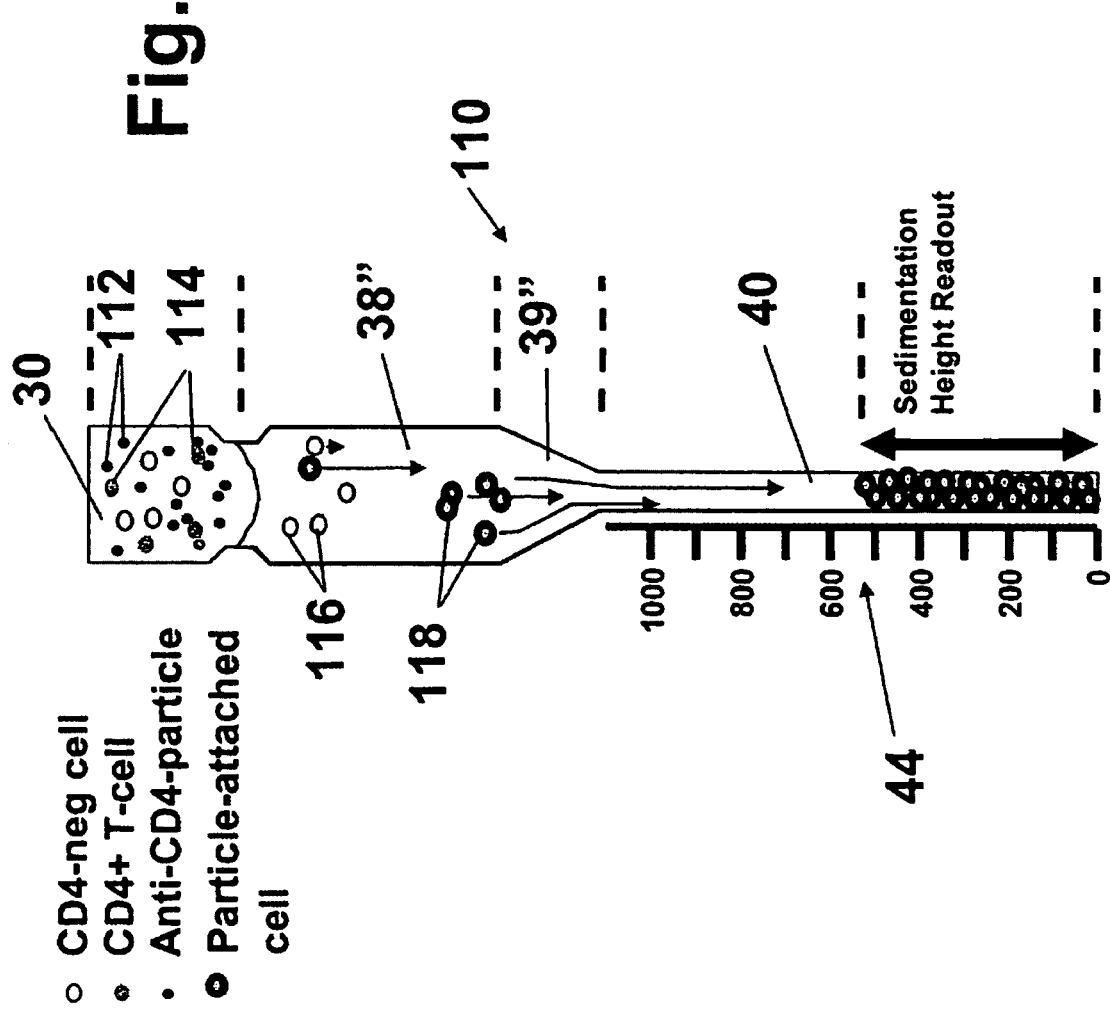
FIG. 6 illustrates the use of an assay device in accordance with the invention used for detecting threshold levels of CD4+ cells in an individual.

The assay device employed in the assay is shown in FIG. 6. The device, indicated at 110, includes, analogous to the device described with respect to FIGS. 1 and 2, a sample chamber 30 in fluid communication, in an upstream-to-downstream direction, a sedimentation chamber 38", and focusing chamber 39" (collectively, an interface chamber), and a collection tube 40, where collection regions in the collection tube are indicated by markings 44 along the length of the tube. The device is assumed to have been pre-filled with a selected-density medium, filling the interface and collection chambers. The sample chamber may contain a selected volume of a suspension of detectable particles capable of reacting specifically with the CD4+ antigen of CD4+ T cells, or alternatively, the particles may be supplied separately, for mixing with the sample prior to addition to the sample chamber As a first step in the assay, a blood fluid sample is taken from the patient. Before application of the sample to the device, RBCs in the sample may be partially or completely removed e.g., by lysis, antibody precipitation, centrifugation to specifically remove RBCs, or centrifugation to pellet all blood cells followed by resuspension of the white-cell fraction, according to methods well known in laboratory hematology. In any event, the final white-blood cell sample is adjusted in volume to correspond to a known volume of the original blood sample.

The sample containing white cells is applied at a given volume to the sample chamber in the device, and the cells are allowed to react with the cell-binding particles for a period, e.g., 10 minutes, sufficient to complete the reaction. Alternatively, this reaction is carried out in a separate tube, then added in combination to the sample chamber. In the device shown in FIG. 6, CD4+ binding particles are indicated as small solid circles at 112, CD4+ positive cells by shaded circles at 114, CD4+ negative cells as open circles at 116, and particle bound CD4+ cells, as shaded circles with a dark particle coating, representing bound particles. As indicated above, the particle-bound cells have a substantially increased density, and are preferably easily detectable by the naked eye.

The cells in the sample are now allowed to sediment under gravitational force through a sedimentation medium having a density less than that of the particle-attached cells into a collection chamber having a plurality of collection regions, e.g., by placing the device in an upright position or in a low-speed centrifuge, until substantially all of the particle-bound cells have settled in the collection tube. FIG. 6 shows the sedimentation process before completion, when some particle-bound cells have yet to settle in the collection tube.

Once sedimentation is complete, the device is inspected, preferably by visual inspection, for the presence of particle-attached cells in at least one selected collection region. In the device illustrated, the collection regions represent incremental segments of the tube corresponding to markings 44 along the side of the tube, corresponding roughly to increments to 100 cells/µl for each marking.

As a final step in the method, a determination is made, based on the number of collection regions filled or partially filled, of whether the added sample volume contains a selected threshold number of cells of the cell type being assayed. In the present illustration, it is seen that the cell count in the assay, at completion, will be above 500 cells/µl, indicating that the individual tested has a normal functioning immune system.

Figure 7:
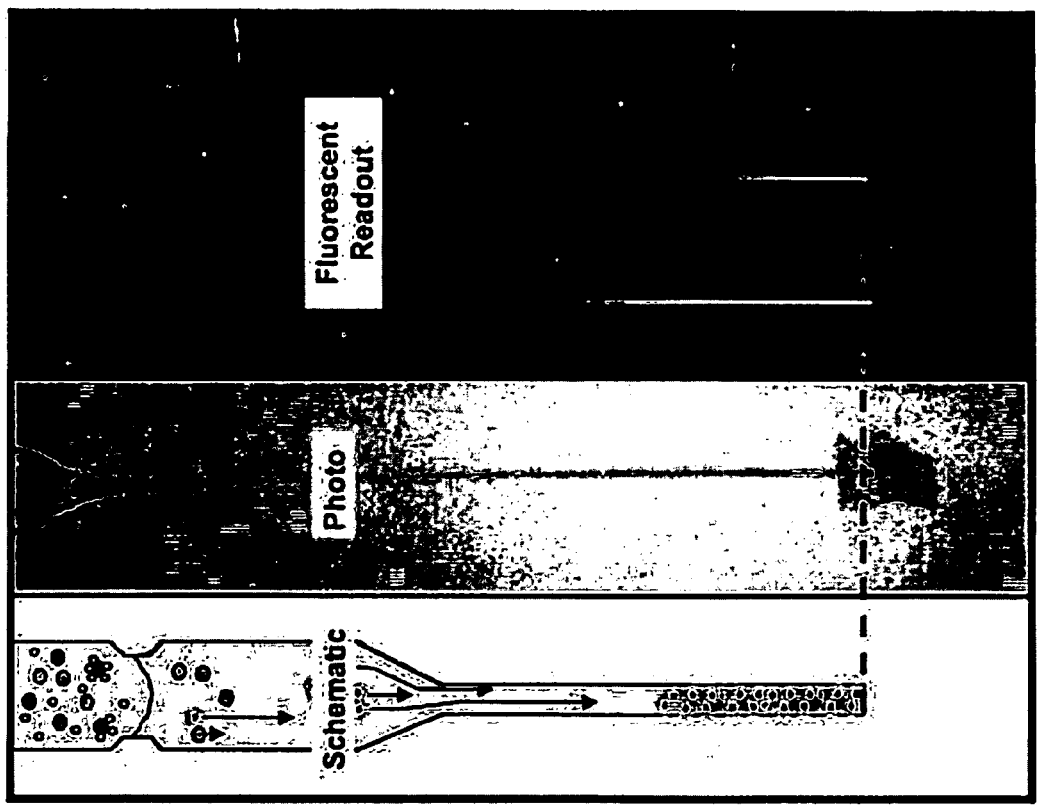
FIGS. 7A-7C show the end point of an assay operation carried out in accordance with the method of the invention, in schematic view (7A), photographic image (7B), and Fluorescent readout (7C)

FIGS. 7A-7C illustrate the results of an exemplary assay method as seen schematically (7A), by photograph (7B), and by fluorescence readout (7C). The fluorescence readout was obtained using fluorescent labeling of PBMC (peripheral blood mononuclear cells) for two different samples, one containing $7.6 \times 10^5$ cells applied (left lane in FIG. 7C) and $7.6 \times 10^4$ cells applied (right lane in FIG. 7C). As seen in the figure, the sample with the greater cell volume produced a more than 2-fold greater a plug height in the assay collection tube.

Figure 8:
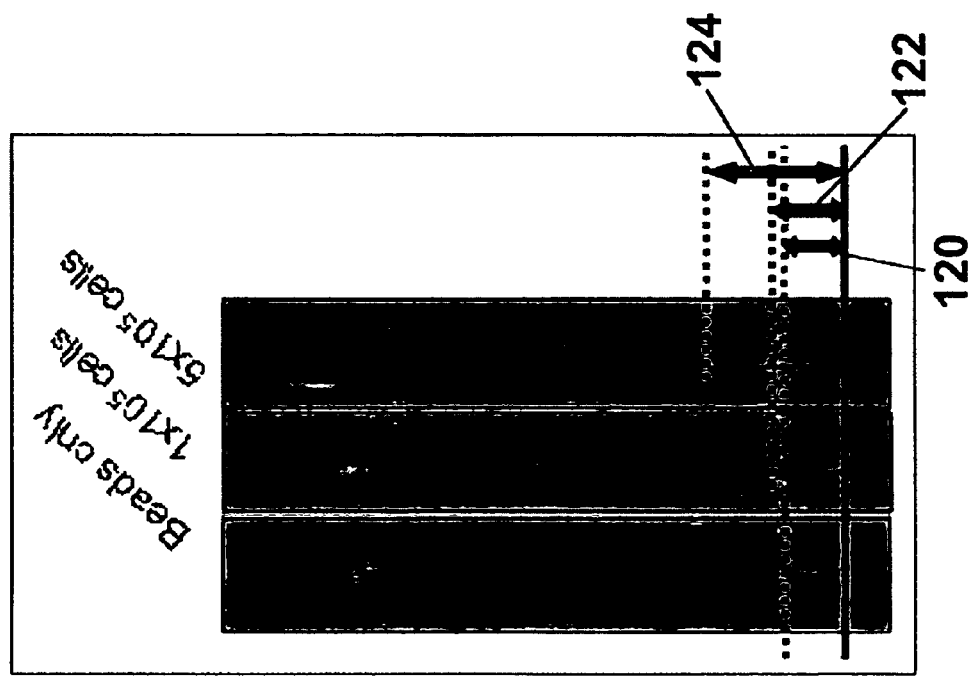
FIG. 8 shows end-point results in the assay method of the invention, for beads alone (left lane), and $1 \times 10^5$ cells, middle lane, and $5 \times 10^5$ cells (right lane)

FIG. 8 shows results from a cell assay in which column heights for samples containing bead alone (left lane), beads plus $1 \times 10^5$ CD4+ cells (center lane, and bead plus $5 \times 10^5$ CD4+ cells. The sedimenting beads alone produced a column height indicated at 120 in the figure. The addition of $1 \times 10^5$ cells increased the height by a small increment, indicated at 122; and the addition of $5 \times 10^5$ cells increased the height by an increment, indicated at 124, that is roughly five times that of the smaller-cell count sample, as expected.

Other applications for monitoring white blood cells as an indicator of a health or treatment condition include, but are not limited to:

Detecting or monitoring the concentration of leukocytes in a blood sample from an individual who may have an infection or other condition leading to an elevation of leukocytes in the blood. In this application, the cells are reacted with particles having surface-bound anti-leukocyte binding agent, such as CD45, and the indicium or indicia that correspond to the threshold collection region(s) of interest indicate a concentration of leukocytes of greater than about 10,000 cells/µl blood.

Detecting or monitoring the concentration of leukocytes in a blood sample from an individual who may depressed numbers of leukocytes in the blood, due to chemotherapy, radiation therapy or leukemia. In this application, the cells are reacted with particles having surface-bound anti-leukocyte binding agent, such as CD45, and the and the indicium or indicia that correspond to the threshold collection region(s) of interest indicate a concentration of leukocytes of less than about 4,000 cells/µl blood.

Detecting or monitoring the concentration of neutrophils in a blood sample from an individual who may depressed numbers of neutrophils in the blood, due to chemotherapy or interferon therapy. In this application, the cells are reacted with particles having surface-bound anti-neutraphile binding agent, such as CD16, and the indicium or indicia that correspond to the threshold collection region(s) of interest indicate a concentration of neutrophils in a selected range between 500 and 2,500 cells/µl blood.

Detecting or monitoring the concentration of bacterial cells in a body-fluid sample from an infected individual, as an indicator of the extent and type of infection. In this application, the cells are reacted with particles having a surface-bound binding agent capable of binding specifically to one or more selected bacterial-wall antigens, and the and the indicium or indicia that correspond to the threshold collection region(s) of interest indicate a detectable concentration of bacterial cells in the blood sample.

From the foregoing, it can be seen how various objects and features of the invention are met. The principle of the assay and device is based on preferential migration of particle-bound cells in a special microcapillary or ladder-type cell-collection arrangement. The device is calibrated in such a way that cell stacking height or number of filled collection regions corresponds to cell count, particularly when adjusted for particle volume. This method does not require antibody coating of device surfaces, and the readout can be achieved by the unaided eye without any additional staining step or reader instrumentation. Thus the method combines the accuracy of cell counting in a hemacytometer with the ease of an unambiguous and simple, reader-less read-out. Due to its simplicity, this method may be ideally suited for the rough environmental conditions in some of the developing countries.

Although the invention has been described with respect to particular embodiments and examples, it will be appreciated that various changes and modifications may be made without departing from the spirit of the invention.

It is claimed:

1. A method for assaying a cell sample to determine a concentration of cells of a given type in the sample, comprising:
    (a) adding to a cell sample containing cells of the given cell type, a given quantity of particles which specifically react and bind to the given type of cells, and being effective, when bound to the cells, to allow particle-bound cells and free particles to be separated from non-particle bound cells in the sample based on their greater density or magnetic susceptibility, which allows them to migrate selectively through a selected medium under the influence of force acting on the particles,
    (b) causing the particle-bound cells and particles in the cell sample to migrate through a microchannel column containing the selected medium, by subjecting the sample to such force for a period of time sufficient to cause the particle-bound cells and particles, but not non-particle-bound cells, to migrate to the bottom of the column, where the added particles make an appreciable contribution to the volume of the particle-bound cells and particles that migrate to the bottom of the column, and account for a known volume in the column, and
    (c) determining the volume of cells of the given type in the sample by measuring the column height of particle-bound cells and particles that migrated to the bottom of the column in step (b), where the measured column height is adjusted by the known volume of particles in the column, and where the volume determined from the adjusted column height equates to the concentration of cells of the given type in the sample.

2. The method of claim 1, wherein said particles, when attached to the cells in step (a) are effective to label the cells with a detectable reporter, and said determining includes visually inspecting the microchannel column for the presence of cells labeled with the detectable reporter.

* * * * *